United States Patent [19]

Nicholas Marchiani Chatelain et al.

[11] Patent Number: 4,874,033
[45] Date of Patent: Oct. 17, 1989

[54] RAPID WARMER FOR BLOOD AND BLOOD PRODUCTS

[76] Inventors: Marie L. Nicholas Marchiani Chatelain, Le Lesdiguères, Résidence St. Mury 38240, Meylan, France, F-38240; Jean-Pierre Pellini, Tèche, Vinay, France, F-38470

[21] Appl. No.: 124,611

[22] Filed: Nov. 24, 1987

[30] Foreign Application Priority Data

Nov. 28, 1986 [FR] France .................................. 86 16859

[51] Int. Cl.[4] .......................... A61M 1/36; A61F 7/00
[52] U.S. Cl. ........................................ 165/1; 165/11.1; 165/32; 165/47; 165/71; 165/80.5; 236/12.11; 604/113; 128/400; 422/44
[58] Field of Search ................ 128/399, 400; 604/113, 604/114; 422/44; 236/12.11, 12.12; 354/299, 328; 165/80.5, 71, 32, 1, 11.1

[56] References Cited

U.S. PATENT DOCUMENTS

| 1,329,426 | 2/1920 | Muckle | 165/80.5 |
| 2,028,471 | 1/1936 | Parent et al. | 165/71 |
| 2,137,676 | 11/1938 | Martin | 165/80.5 |
| 2,254,994 | 9/1941 | Butland | 165/32 |
| 2,741,171 | 4/1956 | Morrison | 354/328 |
| 2,845,929 | 8/1958 | Strumia | 604/113 |
| 3,019,717 | 2/1962 | Gacki | 354/299 |
| 3,064,649 | 11/1962 | Fuson . | |
| 3,352,489 | 11/1967 | Coulombe et al. | 236/12.11 |
| 4,597,435 | 7/1986 | Fosco, Jr. | 165/80.5 |

FOREIGN PATENT DOCUMENTS

| 827702 | 1/1952 | Fed. Rep. of Germany | 604/113 |
| 2515889 | 10/1976 | Fed. Rep. of Germany . | |
| 2937068 | 4/1981 | Fed. Rep. of Germany | 354/299 |
| 3502095 | 7/1986 | Fed. Rep. of Germany . | |
| 538036 | 6/1922 | France | 604/113 |
| 1140895 | 8/1957 | France . | |
| 853994 | 11/1960 | France | 422/44 |

OTHER PUBLICATIONS

Hanney, D. and Waldram, J. M., "Controlled Temperature Equipment for an Experimental Dark Room", The Photography Journal, vol. 91B, 1951, pp. 88–90.

Primary Examiner—John Ford
Attorney, Agent, or Firm—Oliff & Berridge

[57] ABSTRACT

Device for warming or defrosting products for injection or perfusion, particularly blood products, contained in hermetically sealed bottles or bags (10), comprising a cell (1), means making it possible to continuously introduce temperature-controlled water into the cell and possessing at least one inlet line (4) in which are fitted an adjustable thermostatic tap (2) connected on the one hand to a cold water distribution network (2a) and on the other hand to a hot water distribution network (2b), and a flow control valve (3), the cell being provided in its upper part with at least one overflow (5) for the flow of water, such that at least one bag or bottle (10) of product arranged in the cell (1) is submerged, the temperature-controlled water circulating around the bag or bottle.

17 Claims, 1 Drawing Sheet

U.S. Patent    Oct. 17, 1989    4,874,033
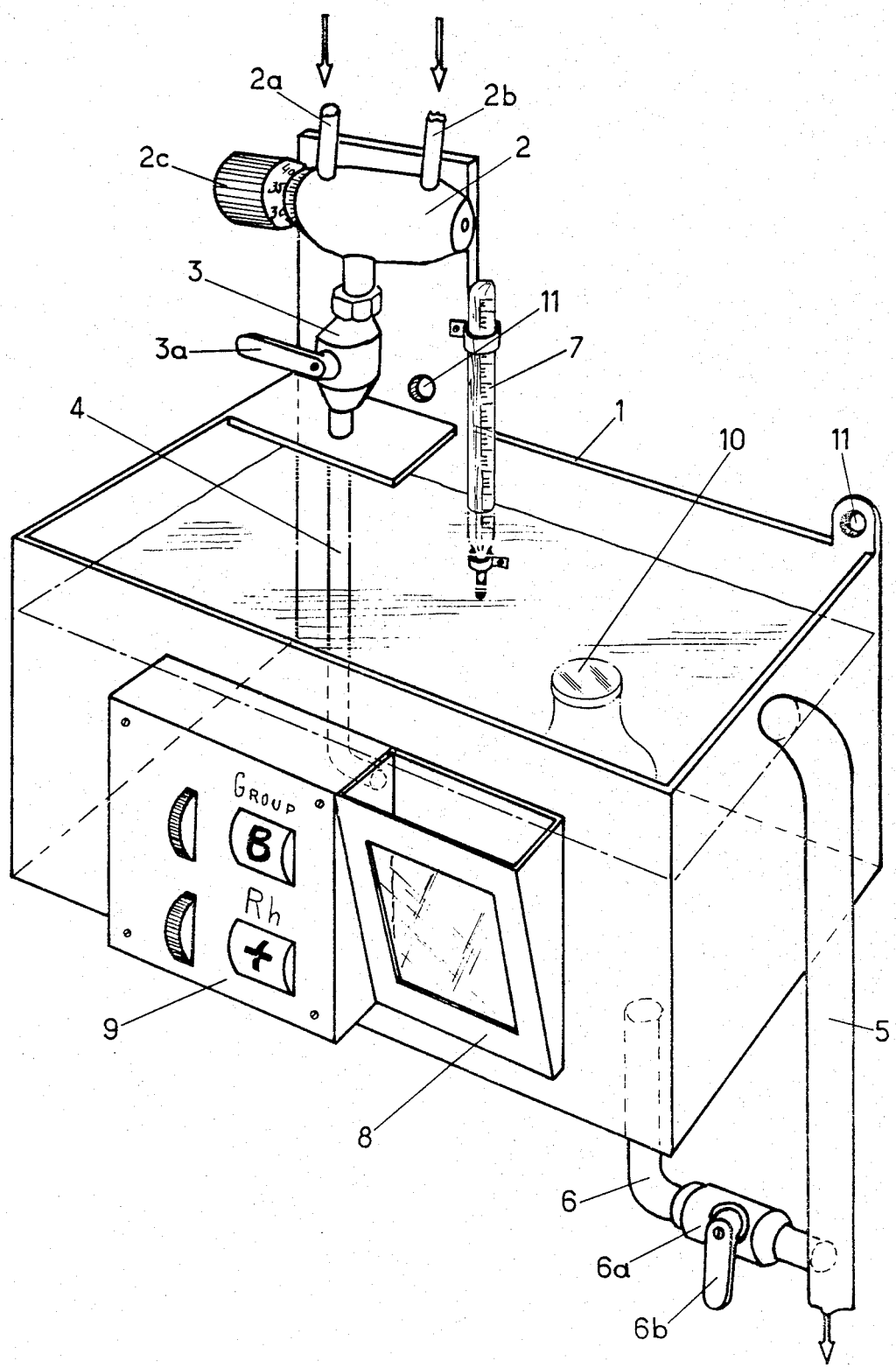

RAPID WARMER FOR BLOOD AND BLOOD PRODUCTS

BACKGROUND OF THE INVENTION

The present invention relates to a device for warming or defrosting products for injections or perfusion, particularly blood products, contained in hermetically sealed bottles or bags, in order to permit injection or transfusion thereof, particularly in the event of extensive loss of blood in the course of surgical intervention in operating theatres.

The warming or defrosting of blood products, in particular, is generally carried out by putting the products in a receptacle which is filled with more or less hot water, without temperature control, the operation being repeated several times. The process is slow and entails risks of impairment of the products. Another method consists of using an electric warmer through which passes a pipe in which the products to be warmed circulate. When the speed of transfusion has to be rapid, the products passing through the electric warmer do not have time to warm.

SUMMARY OF THE INVENTION

The present invention aims to remedy the above disadvantages, and proposes a device which, although very simple, makes it possible to warm or defrost products for injection or perfusion, particularly blood products, quickly and with no risk of impairment thereof.

The device according to the present invention comprises a cell, means making it possible to introduce temperature-controlled water continuously into the cell and possessing at least one inlet line in which are fitted an adjustable thermostatic tap connected on the one hand to a cold water distribution network and on the other hand to a hot water distribution network and a flow control valve, the cell being provided in its upper part with at least one overflow for draining the water, such that at least one bag or bottle of products provided in the cell is submerged, the temperature-controlled water circulating around the bag or bottle.

Preferably, the said inlet line for temperature-controlled water opens into the lower part of the said cell. The outlet of this line and said overflow may advantageously be situated at opposed points in the said cell.

The device according to the present invention preferably comprises a drainage line for the cell in which a valve is fitted. Moreover, the overflow is preferably formed by a flow line connected to this drainage line.

In accordance with the present invention, the said means for supplying temperature-controlled water and said lines are preferably fitted on the cell in a manner such as to form an assembly, this assembly comprising means for its attachment to the cell.

The device according to the present invention preferably bears an indicator making it possible to indicate the nature of the products introduced into the cell, together with means capable of receiving the specification card for the patient for whom these products are intended.

The present invention will be better understood from a study of a device for warming or defrosting products for injection or perfusion, particularly blood products, contained in hermetically sealed bottles or bags, which device is described below by way of non-limiting example and is illustrated in the single attached figure.

BRIEF DESCRIPTION OF THE DRAWING

The sole FIGURE is a perspective view of a preferred embodiment of the present invention.

DETAILED DESCRIPTION OF THE PREFERRED EMBODIMENT

The device shown in the FIGURE comprises a cell 1, preferably of stainless steel and in the shape of a parallelepiped. This cell 1 can be supplied or filled with temperature-controlled water via a thermostatic tap 2, adjustable by means of a switch 2c for example up to a maximum of 40°, and a flow control valve 3 operable by lever 3a. This tap 2 and this valve 3 are, in the example, fitted in succession in a vertical line 4 which descends into the cell 1 to the vicinity of the bottom thereof, the thermostatic tap 2 and the valve 3 being above the cell and being fitted on a plate 1a which extends upwards from the rear wall of the cell 1. The thermostatic tap 2 is connected, by its two inlets 2a and 2b, on the one hand to a cold water distribution network and on the other hand to a hot water distribution network of the building or the room in which the device is installed. The water introduced into the cell 1 can emerge therefrom via an overflow, comprising in the example a vertical evacuation line 5 whose angled upper end opens into the cell 1 in its upper part, its position determining the level of water in the cell 1.

The cell 1 is likewise provided in its lower part with a drainage line 6 in which is fitted a valve 6a provided with a switch 6b. The line 5 and the line 6 are, moreover, connected one to the other in order to drain the water, for example into the building's drainage system, preferably by means of a siphon (not shown).

The device described above functions in the following manner. The valve 6a of the drainage line 6 being closed, the temperature control switch 2c of the thermostatic tap 2 is adjusted to the desired temperature and the valve 3 is opened via lever 3a. The water, controlled to the desired temperature by mixing the cold water coming from the cold water distribution network through the line 2a and the hot water coming from the host water distribution network through the line 2b arrives at the bottom of the cell 1 through the vertical line 4, without causing splashing. The flow rate of water introduced into the cell is controlled by the valve 3.

When the level of the temperature-controlled water reaches the upper inlet of the line 5, the excess is evacuated through this line. In this manner, the temperature-controlled water circulates continuously in the cell 1 at the flow rate controlled by the valve 3. The outlet of the temperature-controlled water inlet line 4 and the upper inlet of the evacuation line 5 being situated at opposing points in the cell 1, the water does not stagnate in any part of the cell 1.

Preferably, when the temperature of the water circulating in the cell 1 is at the set value, it being possible to monitor this temperature by means of a thermometer 7 positioned vertically, the bottle or bag 10 of products for injection or perfusion, particularly blood products which it is desired to warm or defrost, is introduced into the cell 1 in a manner such that the said bottle or bag is preferably completely submerged, the temperature-controlled water circulating continuously around the bottle or the bag 10. When the product contained in the bottle or the bag 10 is warmed or defrosted, it is removed and the products can then be used. Preferably, after each operation, the inlet valve 3 is closed and the drainage valve 6a is opened in a manner such as to empty the cell 1 completely of the water which it contains.

It may be seen that, on the front face of the cell 1, there are provided on the one hand a receptacle 8 into which can be introduced the specification card for the patient for whom the products which are being warmed or defrosted are intended and an indicator 9 with rollers which makes it possible to display the patient's blood group and rhesus factor.

The device which has just been described forms an assembly capable of being fixed, for example, to a wall by screws passing through the apertures 11 in the upper part of the rear wall of the cell 1.

The present invention is not limited to the example of embodiment described above. Numerous alternative embodiments are possible without departing from the scope defined by the attached claims.

We claim:

1. A unitary device for warming or defrosting products for injection or perfusion, particularly blood products, contained in hermetically sealed bottles or bags, comprising:
    an upwardly opened cell for receiving at least one bottle or bag of product;
    means for filling up and obtaining a continuous circulation of water in said cell comprising an inlet line and an overflow outlet line for the water; and
    means for controlling the temperature and the flow rate of the water in said cell,
    said controlling means comprising an adjustable thermostatic tap connectable on the one hand to a cold water distribution network and on the other hand to a hot water distribution network, and an adjustable flow control valve, said adjustable thermostatic tap and said adjustable flow control valve being fitted in said inlet line of the water circulating means,
    said overflow outlet line forming an overflow for draining the water and having an inlet provided at an upper part of said cell,
    the outlet of said temperature controll water inlet line opening into a lower part of said cell adjacent a first lateral side of said cell, the inlet of said overflow outlet line being located adjacent a second lateral side of said cell opposite said first lateral side,
    whereby at least one bottle or bag of product introduced into said cell is submergable by temperature controlled water continuously circulating around the at least one bag or bottle.

2. A unitary device according to claim 1, further comprising a drainage line having its inlet at the lower part of said cell, and a valve.

3. A unitary device according to claim 2, wherein said drainage line is connected to said overflow outlet line.

4. A unitary device according to claim 1, further comprising an indicator for indicating the characteristics of the products introduced into the cell, and means for receiving a specification card of a patient for whom the products are intended.

5. A unitary device according to claim 1, further comprising means for its attachment to a wall.

6. A unitary device according to claim 2, further comprising means for its attachment to a wall.

7. A unitary device according to claim 4, further comprising means for its attachment to a wall.

8. A process for warming or defrosting products for injection or perfusion, particularly blood products, contained in hermetically sealed bottles or bags, comprising the steps of:
    filling up and continuously circulating water in an upwardly opened cell by water circulating means comprising an inlet line and an overflow outlet line;
    controlling the temperature and the flow rate of the water by means of an adjustable thermostatic tap connectable on the one hand to a cold water distribution network and on the other hand to a hot water distribution network, and an adjustable flow control valve, said adjustable thermostatic tap and said adjustable flow control valve being fitted in said inlet line of the water circulating means, said overflow outlet line forming an overflow for draining the water and having an inlet provided at an upper part of said cell, the outlet of said temperature controlled water inlet line opening into a lower part of said cell adjacent a first lateral side of said cell, the inlet of said overflow outlet line being located adjacent a second lateral side of said cell opposite said first side;
    introducing at least one bottle or bag of product into said cell such that said at least one bottle or bag of product is submerged by the temperature controlled water continuously circulating around the at least one bottle or bag; and
    removing the at least one bottle or bag of product from the cell when the product contained therein is warmed or defrosted.

9. A process according to claim 8, further comprising the steps of closing said flow control valve and draining the water out of said cell, the drainage means comprising a drainage line having its inlet at the lower part of said cell, and a valve.

10. A process according to claim 8, further comprising the steps of indicating the characteristics of the product introduced into the cell and the specification of the patient for whom these products are intended.

11. A process according to claim 9, further comprising the steps of indicating the characteristics of the product introduced into the cell and the specification of the patient for whom these products are intended.

12. A unitary device for warming or defrosting products for injection or perfusion, particularly blood products, contained in hermetically sealed bottles or bags, comprising:
    an upwardly opened cell for receiving at least one bottle or bag of products;
    means for filling up and obtaining a continuous circulation of water in said cell so that said at least one bottle or bag of product placed in the cell is submerged and the water circulates around said at least one bottle or bag;
    means for controlling the temperature and the flow rate of the water in said cell;
    an indicator for indicating the characteristics of the products introduced into the said cell; and
    means capable of receiving a specification card of a patient for whom the products are intended.

13. A unitary device according to claim 12, wherein said controlling means comprise an adjustable thermostatic tap connectable on the one hand to a cold distribution network and on the other hand to a hot water distribution network, and an adjustable flow control valve, said adjustable thermostatic tap and said adjustable flow control valve being fitted in an inlet line of the water circulating means, said water circulating means comprising an overflow outlet line provided at an upper part of said cell and forming an overflow for draining the water, the outlet of said temperature controlled water inlet line opening into a lower part of said cell adjacent a first lateral side of said cell, the inlet of said overflow outlet line being located adjacent a second lateral side of said cell opposite said first lateral side.

14. A unitary device according to claim 13, further comprising a drainage line having its inlet at the lower part of said cell, and a valve.

15. A unitary device according to claim 12, further comprising means for its attachment to a wall.

16. A unitary device according to claim 13, further comprising means for its attachment to a wall.

17. A process for warming or defrosting products for injection or perfusion, particularly blood products, contained in hermetically sealed bottles or bags, comprising the steps of:

filling up and continuously circulating water in an upwardly opened cell;

controlling the temperature and the flow of the water to achieve a desired temperature and flow rate in the cell;

introducing at least one bottle or bag of product into said cell such that said at least one bottle or bag is submerged and the water circulates around it; and indicating on the cell the characteristics of the product introduced into the cell and receiving a specification card of the patient for whom the product is intended.

* * * * *